(12) United States Patent
Rowland et al.

(10) Patent No.: US 8,097,731 B2
(45) Date of Patent: Jan. 17, 2012

(54) REACTION PRODUCTS OF MERCAPTOBENZOTHIAZOLES, MERCAPTOTHIAZOLINES, AND MERCAPTOBENZIMIDALZOLES WITH EPOXIDES AS LUBRICANT ADDITIVES

(75) Inventors: Robert G. Rowland, Woodbridge, CT (US); Ronald D. Abbott, New Hartford, CT (US)

(73) Assignee: Crompton Corporation, Middlebury, CT (US)

( * ) Notice: Subject to any disclaimer, the term of this patent is extended or adjusted under 35 U.S.C. 154(b) by 780 days.

(21) Appl. No.: 12/208,192

(22) Filed: Sep. 10, 2008

(65) Prior Publication Data

US 2009/0076279 A1 Mar. 19, 2009

Related U.S. Application Data

(62) Division of application No. 10/888,137, filed on Jul. 8, 2004, now Pat. No. 7,442,673.

(60) Provisional application No. 60/495,117, filed on Aug. 15, 2003.

(51) Int. Cl.
*C07D 277/16* (2006.01)
*C07D 277/74* (2006.01)

(52) U.S. Cl. ........................ 548/169; 548/186

(58) Field of Classification Search .................. 548/169, 548/186
See application file for complete search history.

(56) References Cited

U.S. PATENT DOCUMENTS

| | | |
|---|---|---|
| 2,414,257 A | 1/1947 | Evans et al. |
| 3,174,933 A | 3/1965 | Klein et al. |
| 3,215,641 A | 11/1965 | Rocklin et al. |
| 3,293,181 A | 12/1966 | Stuart |
| 3,396,109 A | 8/1968 | Butler |
| 3,397,145 A | 8/1968 | Cyba |
| 3,442,804 A | 5/1969 | Le Suer |
| 3,637,499 A | 1/1972 | Pollak |
| 5,062,977 A | 11/1991 | Germanaud et al. |
| 5,084,195 A | 1/1992 | Camenzind et al. |
| 5,300,243 A | 4/1994 | Camenzind et al. |
| 5,498,809 A | 3/1996 | Emert et al. |
| 5,512,190 A | 4/1996 | Anderson et al. |
| 5,514,189 A | 5/1996 | Farng et al. |
| 5,892,051 A | 4/1999 | Wirth et al. |
| 6,100,406 A | 8/2000 | Camenzind et al. |
| 6,187,726 B1 | 2/2001 | Nalesnik et al. |
| 6,255,259 B1 | 7/2001 | Camenzind et al. |
| 6,551,996 B1 | 4/2003 | Schwartz et al. |
| 6,559,107 B2 | 5/2003 | Nalesnik |
| 6,566,311 B1 | 5/2003 | Nalesnik |

FOREIGN PATENT DOCUMENTS

EP 0894793 3/1999

OTHER PUBLICATIONS

Di Nunno, et al.: "Baker's yeast-induced asymmetric reduction of alphaketosulfides: synthesis of optically active 1-(benzothizol-2-ylsulfanyl)-2-alkanols, 2-alkanols, and thiiranes" Tetrahedron Asymmetry, vol. 10, No. 10, 1999, pp. 1913-1926.
Written Opinion of the International Searching Authority for PCT/US2004/025027 received Nov. 24, 2004, 4 pages.
Zhang et al., Elsevier Science S.A., Wear, 1999, 224(1), pp. 50-55.

*Primary Examiner* — Laura L. Stockton
(74) *Attorney, Agent, or Firm* — Joseph Suhadolnik

(57) ABSTRACT

A composition comprising:
(A) a lubricant, and
(B) at least one alcohol that is the reaction product of mercaptobenzothiazoles, mercaptothiazolines, or mercaptobenzimidazoles with various epoxies.

7 Claims, No Drawings

REACTION PRODUCTS OF MERCAPTOBENZOTHIAZOLES, MERCAPTOTHIAZOLINES, AND MERCAPTOBENZIMIDALZOLES WITH EPOXIDES AS LUBRICANT ADDITIVES

This application is a divisional of U.S. patent application Ser. No. 10/888,137, filed Jul. 8, 2004, now U.S. Pat. No. 7,442,673, which claims priority to Provisional Application No. 60/495,117, filed Aug. 15, 2003. The contents of these applications and patent are incorporated herein by reference in their entireties.

BACKGROUND OF THE INVENTION

1. Field of the Invention

This invention is related to lubricants, especially lubricating oils, and, more particularly, to a class of ashless and non-phosphorus-containing anti-wear additives derived from alcohols that are the reaction products of mercaptobenzothiazoles, mercaptothiazolines, or mercaptobenzimidazoles with various epoxides.

2. Description of Related Art

In developing lubricating oils, there have been many attempts to provide additives that impart antifatigue, anti-wear, and extreme pressure properties thereto. Zinc dialkyldithiophosphates (ZDDP) have been used in formulated oils as antiwear additives for more than 50 years. However, zinc dialkyldithiophosphates give rise to ash, which contributes to particulate matter in automotive exhaust emissions, and regulatory agencies are seeking to reduce emissions of zinc into the environment. In addition, phosphorus, also a component of ZDDP, is suspected of limiting the service life of the catalytic converters that are used on cars to reduce pollution. It is important to limit the particulate matter and pollution formed during engine use for toxicological and environmental reasons, but it is also important to maintain undiminished the antiwear properties of the lubricating oil.

In view of the aforementioned shortcomings of the known zinc and phosphorus-containing additives, efforts have been made to provide lubricating oil additives that contain neither zinc nor phosphorus or, at least, contain them in substantially reduced amounts.

Illustrative of non-zinc, i.e., ashless, non-phosphorus-containing lubricating oil additives are the reaction products of 2,5-dimercapto-1,3,4-thiadiazoles and unsaturated mono-, di-, and tri-glycerides disclosed in U.S. Pat. No. 5,512,190 and the dialkyl dithiocarbamate-derived organic ethers of U.S. Pat. No. 5,514,189.

U.S. Pat. No. 5,512,190 discloses an additive that provides antiwear properties to a lubricating oil. The additive is the reaction product of 2,5-dimercapto-1,3,4-thiadiazole and a mixture of unsaturated mono-, di-, and triglycerides. Also disclosed is a lubricating oil additive with antiwear properties produced by reacting a mixture of unsaturated mono-, di-, and triglycerides with diethanolamine to provide an intermediate reaction product and reacting the intermediate reaction product with 2,5-dimercapto-1,3,4 thiadiazole.

U.S. Pat. No. 5,514,189 discloses that dialkyl dithiocarbamate-derived organic ethers have been found to be effective antiwear/antioxidant additives for lubricants and fuels.

U.S. Pat. Nos. 5,084,195 and 5,300,243 disclose N-acyl-thiourethane thioureas as antiwear additives specified for lubricants or hydraulic fluids.

The reaction of mercaptobenzothiazole (MBT) with epoxides is taught in the family of patents by Camenzind et. al. (EP 0 894 793; U.S. Pat. No. 6,100,406; U.S. Pat. No. 6,255,259). Example 1 in U.S. Pat. No. 6,255,259 teaches reacting MBT with propylene oxide. However, the resulting intermediate is not recognized by Camenzind as having utility as a lubricant additive in its own right. Rather, it is reacted further with a phenolic antioxidant compound to form a mixed phenolic/MBT additive. The same can be said for Example 12, where glycidal neodecanoate (Glydexx® N-10) is reacted with MBT, but the product again is reacted further with a phenolic antioxidant derivative. The intermediates are not shown to have been tested for anti-wear performance.

This multi-step process is disadvantageous, as the additional reaction steps must result in higher processing costs and added undesirable waste.

Zhang et al (*Wear*, 1999, 224(1), 50-55) evaluated a dithiocarbamate as a lubricant additive where a glycidaldithiocarbamate is linked to a benzothiazoylthio moiety.

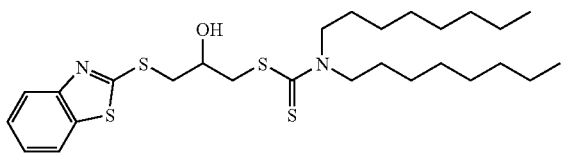

Zhang et al. improved the solubility of MBT in oil by introducing the dialkyl dithiocarbamate group. The dithiocarbamate group has long been known to have anti-wear and extreme pressure activity. However, dithiocarbamates can also be undesirable, as they are corrosive towards copper, and attack engine seals. Furthermore, the dithiocarbamate group contributes additional sulfur content to the additive. This is not desirable in light of recent trends towards lower sulfur lubricants, which are in turn being driven by government requirements for lower sulfur fuels.

Neither Camenzind nor Zhang discloses or suggests that reacting mercaptobenzothiazole with an epoxide that does not contain an additional functional group that is known to possess utility as a lubricant additive will result in an additive with superior anti-wear performance.

U.S. Pat. No. 6,187,726 discloses compounds and lubricant compositions that comprise a substituted linear thiourea of the structure

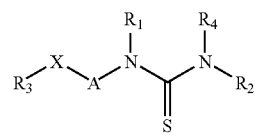

wherein $R_1$, $R_2$, and $R_4$ are independently selected from the group consisting of alkyl, alkenyl, aryl, alkaryl, aralkyl, and hydrogen; $R_3$ is selected from the group consisting of alkyl, alkenyl, and combinations thereof; X is selected from the group consisting of (i) methylene, if, and only if, $R_3$ is alkylene, (ii) oxygen, and (iii) sulfur; and A is selected from the group consisting of alkylene and aryl.

U.S. Pat. No. 6,551,966 discloses a composition comprising:
(A) a lubricant, and
(B) at least one 5-alkyl-2-mercapto-1,3,4-oxadiazole compound of the formula:

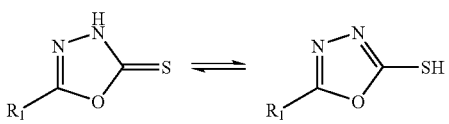

wherein $R_1$ is a hydrocarbon or functionalized hydrocarbon of from 1 to 30 carbon atoms.

U.S. Pat. No. 6,559,107 discloses a composition comprising:
(A) a lubricant, and
(B) at least one 5-alkyl-2-thione-1,3,4-thiadiazolidine compound of the formula:

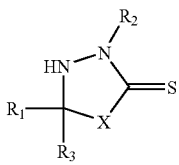

wherein $R_1$ is a hydrocarbon or functionalized hydrocarbon of from 1 to 30 carbon atoms, $R_2$ and $R_3$ are independently selected from the group consisting of hydrocarbon or functionalized hydrocarbons of from 1 to 30 carbon atoms and hydrogen, and X is oxygen, sulfur or nitrogen.

U.S. Pat. No. 6,566,311 discloses a composition comprising: (A) a lubricant, and (B) at least one 1,3,4-oxadiazole compound of the formula:

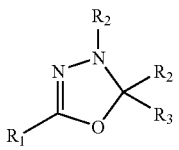

wherein $R_1$ is selected from the group consisting of hydrogen, linear or branched alkyl, alkenyl, alkaryl, aryl, alkyl ether, and alkyl ester; $R_2$, $R_3$, and $R_4$ are independently selected from the group consisting of hydrogen, linear or branched alkyl, alkenyl, alkaryl, and aryl; and any alkyl moiety can optionally contain within it oxygen ether, ester, or amide groups.

The disclosures of the foregoing references are incorporated herein by reference in their entirety.

SUMMARY OF THE INVENTION

As noted above, lubricant anti-wear agents containing phosphorus, such as zinc dithiophosphates, are not compatible with current and future goals for service life of emissions after-treatment devices, such as catalytic converters. It has now been found that thiazoylthio- and imidazolylthio alcohols, the reaction products of mercaptobenzothiazoles, mercaptothiazolines, or mercaptobenzimidazoles with various epoxides, are useful as ashless anti-wear additives for lubricants.

More particularly, the present invention is directed to a composition comprising:
(A) a lubricant, and
(B) at least one compound selected from the group consisting of alcohols of the formulae:

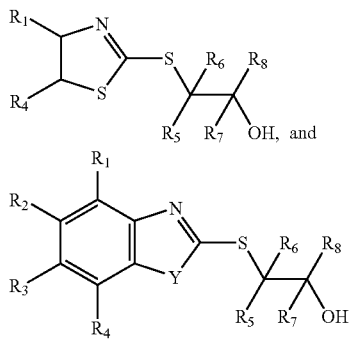

wherein
Y is N or S;
$R_1$, $R_2$, $R_3$, and $R_4$ are independently selected from the group consisting of hydrogen, alkyl, cycloalkyl, alkenyl, alkaryl, aryl, alkoxy, and alkyl ester;
$R_5$ is selected from the group consisting of hydrogen, alkyl, alkoxy, a carboxy alkyl group of the structure:

$(CH_2)_p CO_2 R_9$ where:
p is from 1 to 18, and
$R_9$ is hydrocarbyl;
$R_7$ is selected from the group consisting of hydrogen, $CH_2OR_{11}$, alkyl, and alkenyl, wherein:
said alkyl and alkenyl groups are optionally substituted with OH, oxirane, or X;
$R_{11}$ is selected from the group consisting of alkyl of from 1 to 36 carbon atoms, alkaryl of from 6 to about 50 carbon atoms, and aryl, and may contain ether or ester functionalities;
X is of the structure:

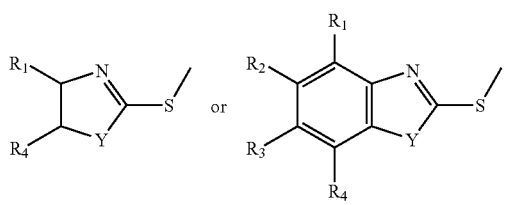

or $R_5$ and $R_7$ are fused together to form a ring of 3-10, preferably 5 or 6, carbon atoms, which may be further substituted with alkyl, cycloalkyl, alkenyl, aryl, or alkoxy groups, and may contain ether or ester functionalities;
and $R_6$ and $R_8$ are independently selected from the group consisting of hydrogen, alkyl, cycloalkyl, alkenyl, aryl, and alkoxy.

DESCRIPTION OF THE PREFERRED EMBODIMENTS

According to the present invention, the reaction products of 2-mercaptobenzothiazole (MBT), 2-mercaptothiazoline, and 2-mercaptobenzimidazole with various epoxides are useful as ashless anti-wear additives for lubricants. As noted above, the present invention is more specifically directed to a composition comprising:

(A) a lubricant, and
(B) at least one compound selected from the group consisting of alcohols of the formulae:

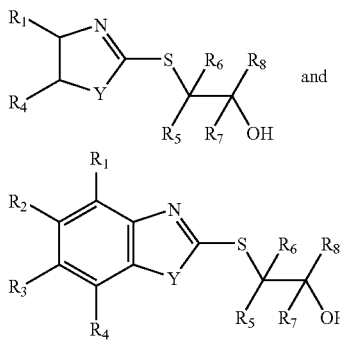

and wherein
Y is nitrogen or sulfur, preferably sulfur;
$R_1$, $R_2$, $R_3$, and $R_4$ are independently selected from the group consisting of hydrogen, alkyl, cycloalkyl, alkenyl, alkaryl, aryl, alkoxy, and alkyl ester, preferably hydrogen;
$R_5$ is selected from the group consisting of hydrogen, alkyl, alkoxy, a carboxy alkyl group of the structure:

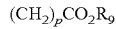

where:
p is from 1 to 18, and
$R_9$ is hydrocarbyl;
$R_1$ is selected from the group consisting of hydrogen, $CH_2OR_{11}$, alkyl, and alkenyl, wherein:
said alkyl and alkenyl groups are optionally substituted with OH, oxirane, or X,
$R_{11}$, is selected from the group consisting of alkyl of from 1 to 36 carbon atoms, alkaryl of from 6 to about 50 carbon atoms, and aryl, and may contain ether or ester functionalities;
X is of the structure:

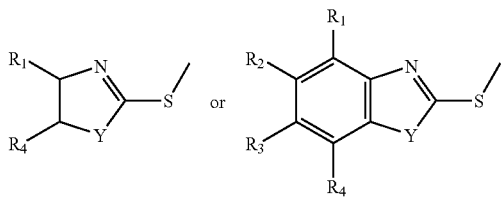

or $R_5$ and $R_7$ are fused together to form a ring of 3-10, preferably 5 or 6, carbon atoms, which may be further substituted with alkyl, cycloalkyl, alkenyl, aryl, or alkoxy groups, and may contain ether or ester functionalities;
and $R_6$ and $R_8$ are independently selected from the group consisting of hydrogen, alkyl, cycloalkyl, alkenyl, aryl, and alkoxy.

It is especially preferred that the lubricant of the present invention be a lubricating oil.

Unless otherwise indicated, it is preferred that in the above description of the alcohols employed in the practice of the present invention, any alkyl or alkenyl groups referred to, or any moieties comprising such groups, e.g., alkoxy groups, have from 1 to 18 carbon atoms.

As employed herein, the term "hydrocarbyl" includes hydrocarbon as well as substantially hydrocarbon groups. "Substantially hydrocarbon" describes groups that contain heteroatom substituents that do not alter the predominantly hydrocarbon nature of the group.

Examples of hydrocarbyl groups include the following:
(1) hydrocarbon substituents, i.e., aliphatic (e.g., alkyl or alkenyl), alicyclic (e.g., cycloalkyl, cycloalkenyl) substituents, aromatic substituents, aromatic-, aliphatic-, and alicyclic-substituted aromatic substituents, and the like, as well as cyclic substituents wherein the ring is completed through another portion of the molecule (that is, for example, any two indicated substituents may together form an alicyclic radical);
(2) substituted hydrocarbon substituents, i.e., those substituents containing non-hydrocarbon groups which, in the context of this invention, do not alter the predominantly hydrocarbon nature of the substituent; those skilled in the art will be aware of such groups (e.g., halo, hydroxy, mercapto, nitro, nitroso, sulfoxy, etc.);
(3) heteroatom substituents, i.e., substituents that will, while having a predominantly hydrocarbon character within the context of this invention, contain an atom other than carbon present in a ring or chain otherwise composed of carbon atoms (e.g., alkoxy or alkylthio). Suitable heteroatoms will be apparent to those of ordinary skill in the art and include, for example, sulfur, oxygen, nitrogen, and such substituents as, e.g., pyridyl, furyl, thienyl, imidazolyl, etc. Preferably, no more than about 2, more preferably no more than one, hetero substituent will be present for every ten carbon atoms in the hydrocarbyl group. Most preferably, there will be no such heteroatom substituents in the hydrocarbyl group, i.e., the hydrocarbyl group is purely hydrocarbon.

In the formula described above, $R_9$ is hydrocarbyl. Examples of $R_9$ include, but are not limited to,
unsubstituted phenyl;
phenyl substituted with one or more alkyl groups, such as methyl, ethyl, propyl, butyl, pentyl, hexyl, heptyl, octyl, nonyl, decyl, isomers of the foregoing, and the like;
phenyl substituted with one or more alkoxy groups, such as methoxy, ethoxy, propoxy, butoxy, pentoxy, hexoxy, heptoxy, octoxy, nonoxy, decoxy, isomers of the foregoing, and the like;
phenyl substituted with one or more alkyl amino or aryl amino groups;
naphthyl and alkyl substituted naphthyl;
straight chain or branched chain alkyl or alkenyl groups containing from one to fifty carbon atoms, including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, oleyl, nonadecyl, eicosyl, heneicosyl, docosyl, tricosyl, tetracosyl, pentacosyl, triacontyl, isomers of the foregoing, and the like; and
cyclic alkyl groups, such as cyclopentyl, cyclohexyl, cycloheptyl, cyclooctyl, and cyclododecyl.

Suitable epoxides for use in the preparation of the alcohols employed in the practice of the present invention include ethylene oxide, propylene oxide, 1,2-epoxybutane, 1,2-epoxypentane, 1,2-epoxyheptane, 1,2-epoxyoctane, 1,2-epoxynonane, 1,2-epoxydecane, 1,2-epoxyundecane, 1,2-epoxydodecane, 1,2-epoxytetradecane, 1,2-epoxyhexadecane, 1,2-epoxyoctadecane, 1,2-epoxyeicosane, cyclohexene oxide, styrene oxide, phenyl propylene oxide, 4-nonylphenyl glycidal ether, butyl glycidal ether, 2-ethylhexyl glycidal ether, $C_8$-$C_{18}$ alkyl glycidal ethers, glycidal hexadecyl ether, o-cresyl glycidal ether, p-tert-butyl phenyl glycidal ether, 1,2-epoxy-2-phenoxy propane, furfuryl glycidal ether, glycidal 4-methoxyphenyl ether, glycidal 2-methylphenyl ether, epoxidized $C_1$-$C_{18}$ esters of unsaturated $C_3$-$C_{36}$ carboxylic acids, particularly epoxidized esters of $C_{12}$-$C_{20}$ acids, such as epoxidized methyl tallate, epoxidized butyl tallate, epoxidized 2-ethylhexyl tallate, epoxidized octyl tallate, and epoxidized methyl oleate, epoxidized butyl oleate, epoxidized 2-ethylhexyl oleate, epoxidized octyl oleate, and the like; epoxidized unsaturated oils, such as epoxidized soybean oil, epoxidized canola oil, and the like. It is expected that under the right conditions suitably soluble derivatives from vinyl cyclohexane diepoxide and glycerol propoxylate triglycidal ether and similar reagents containing more than one epoxide moiety could be prepared to yield functional materials. It is also expected that under the right conditions suitably soluble derivatives could be prepared from 2-mercaptobenzoxazole and epoxide reagents as described herein that would yield functional materials.

It will be apparent to those skilled in the art that under certain conditions one might achieve a substitution on the heterocyclic nitrogen for at least a portion of the reaction mixture, caused by reaction of the epoxide with the nitrogen. To a lesser extent one may also anticipate the production of primary alcohols, caused by substitution of the heterocyclic molecule, especially the mercapto group thereof, at the internal (2-) position of the epoxide (oxirane) group.

Preferred alcohol additives for use in the practice of the present invention include, but are not limited to, 1-(2-benzothiazoylthio)-2-decanol, 1-(2-benzothiazoylthio)-2-dodecanol, 1-(2-benzothiazoylthio)-2-tetradecanol, 1-(2-benzothiazoylthio)-2-hexadecanol, 1-(2-benzothiazoylthio)-2-octadecanol, 2-(2-benzothiazoylthio-cyclohexanol, α-[(2-benzothiazoylthio)methyl]-benzenemethanol, 1-(2-benzothiazoylthio)-3-(4-nonylphenoxy)-propan-2-ol, the reaction product of epoxidized 2-ethylhexyl tallate with mercaptobenzothiazole, the reaction product of epoxidized soybean oil with mercaptobenzothiazole, 2-thiazoylthio-cyclohexanol, 1-thiazoylthio-2-dodecanol, 1-benzimidazoylthio-2-dodecanol, and the like.

Especially preferred alcohol additives for use in the practice of the present invention include those having the following structures:

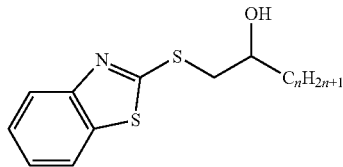

where n=1 to about 36, more preferably 1 to about 18, most preferably 8 to 12;

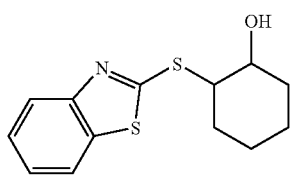

(here, $R_5$ and $R_7$ of the above general formulae have been fused);

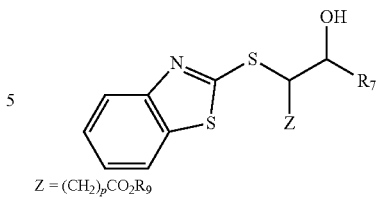

$Z = (CH_2)_pCO_2R_9$ where the group ZCHCH(OH)$R_7$ is a residue from the reaction of mercaptobenzothiazole with an epoxidized unsaturated acid ester, such as an epoxidized ester of oleic, linoleic, linolenic, or eleostearic acid; or an epoxidized tall oil (tallate) ester; tallate and oleate esters being a preferred embodiment, and reaction products of 2-ethylhexyl tallate being particularly preferred; and

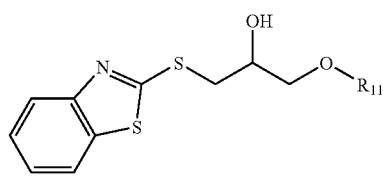

where $R_{11}$ is $C_1$ to about $C_{18}$ alkyl, more preferably $C_{4-12}$, or aryl or alkyl substituted aryl, particularly a $C_8$-$C_{12}$ substituted phenyl, such as nonylphenyl.

The alcohol additives of the present invention can be used as either partial or complete replacements for the zinc dialkyldithiophosphates currently used. They can also be used in combination with other additives typically found in lubricating oils, as well as with other ashless, antiwear additives. The benzothiazoylthio alcohol additives of the present invention may also display synergistic effects with these other typical additives to improve oil performance properties. The additives typically found in lubricating oils are, for example, dispersants, detergents, corrosion/rust inhibitors, antioxidants, antiwear agents, antifoamants, friction modifiers, seal swell agents, demulsifiers, viscosity index (VI) improvers, pour point depressants, and the like. See, for example, U.S. Pat. No. 5,498,809 for a description of useful lubricating oil composition additives, the disclosure of which is incorporated herein by reference in its entirety. Examples of dispersants include polyisobutylene succinimides, polyisobutylene succinate esters, Mannich Base ashless dispersants, and the like. Examples of detergents include metallic phenates, metallic sulfurized phenates, metallic sulfonates, metallic alkyl salicylates, and the like. Examples of antioxidants include alkylated diphenylamines, N-alkylated phenylenediamines, alkylated phenyl α-naphthylamines, hindered phenolics, alkylated hydroquinones, hydroxylated thiodiphenyl ethers, alkylidenebisphenols, oil soluble copper compounds, and the like. Examples of antiwear additives that can be used in combination with the additives of the present invention include organo borates, organo phosphites, organic sulfur-containing compounds, zinc dialkyldithiophosphates, zinc diaryldithiophosphates, phosphosulfurized hydrocarbons, and the like. The following are exemplary of such additives and are commercially available from The Lubrizol Corporation: Lubrizol 677A, Lubrizol 1095, Lubrizol 1097, Lubrizol 1360, Lubrizol 1395, Lubrizol 5139, and Lubrizol 5604, among others. Examples of friction modifiers include fatty acid esters and amides, organo molybdenum sulfurized and unsulfurized compounds, molybdenum dialkylthiocarbamates, molybdenum dialkyl dithiophosphates, and the like. An example of an antifoamant is polysiloxane, and the like. An example of a rust inhibitor is a polyoxyalkylene polyol, and the like. Examples of VI improvers include olefin copolymers and dispersant olefin copolymers, and the like. An example of a pour point depressant is polymethacrylate, and the like.

Representative conventional antiwear agents that can be used include, for example, the zinc dialkyl dithiophosphates and the zinc diaryl dithiophosphates.

Suitable phosphates include dihydrocarbyl dithiophosphates, wherein the hydrocarbyl groups contain an average of at least three carbon atoms. Particularly useful are metal salts of at least one dihydrocarbyl dithiophosphoric acid wherein the hydrocarbyl groups contain an average of at least 3 carbon atoms. The acids from which the dihydrocarbyl dithiophosphates can be derived can be illustrated by acids of the formula:

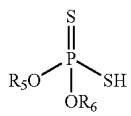

wherein $R_5$ and $R_6$ are the same or different and are alkyl, cycloalkyl, aralkyl, alkaryl or substituted substantially hydrocarbon radical derivatives of any of the above groups, and wherein the $R_5$ and $R_6$ groups in the acid each have, on average, at least 3 carbon atoms. By "substantially hydrocarbon" is meant radicals containing substituent groups (e.g., 1 to 4 substituent groups per radical moiety) such as ether, ester, nitro, or halogen that do not materially affect the hydrocarbon character of the radical.

Specific examples of suitable $R_5$ and $R_6$ radicals include isopropyl, isobutyl, n-butyl, sec-butyl, n-hexyl, heptyl, 2-ethylhexyl, diisobutyl, isooctyl, decyl, dodecyl, tetradecyl, hexadecyl, octadecyl, butylphenyl,o,p-depentylphenyl, octylphenyl, polyisobutene-(molecular weight 350)-substituted phenyl, tetrapropylene-substituted phenyl, beta-octylbutyl-naphthyl, cyclopentyl, cyclohexyl, phenyl, chlorophenyl, o-dichlorophenyl, bromophenyl, naphthenyl, 2-methylcyclohexyl, benzyl, chlorobenzyl, chloropentyl, dichlorophenyl, nitrophenyl, dichlorodecyl and xenyl radicals. Alkyl radicals having from about 3 to about 30 carbon atoms and aryl radicals having from about 6 to about 30 carbon atoms are preferred. Particularly preferred $R_5$ and $R_6$ radicals are alkyl of from 4 to 18 carbon atoms.

The phosphorodithioic acids are readily obtainable by the reaction of phosphorus pentasulfide and an alcohol or phenol. The reaction involves mixing, at a temperature of about 20° C. to 200° C., 4 moles of the alcohol or phenol with one mole of phosphorus pentasulfide. Hydrogen sulfide is liberated as the reaction takes place. Mixtures of alcohols, phenols, or both can be employed, e.g., mixtures of $C_3$ to $C_{30}$ alcohols, $C_6$ to $C_{30}$ aromatic alcohols, etc.

The metals useful to make the phosphate salts include Group I metals, Group II metals, aluminum, lead, tin, molybdenum, manganese, cobalt, and nickel. Zinc is the preferred metal. Examples of metal compounds that can be reacted with the acid include lithium oxide, lithium hydroxide, lithium carbonate, lithium pentylate, sodium oxide, sodium hydroxide, sodium carbonate, sodium methylate, sodium propylate, sodium phenoxide, potassium oxide, potassium hydroxide, potassium carbonate, potassium methylate, silver oxide, silver carbonate, magnesium oxide, magnesium hydroxide, magnesium carbonate, magnesium ethylate, magnesium propylate, magnesium phenoxide, calcium oxide, calcium hydroxide, calcium carbonate, calcium methylate, calcium propylate, calcium pentylate, zinc oxide, zinc hydroxide, zinc carbonate, zinc propylate, strontium oxide, strontium hydroxide, cadmium oxide, cadmium hydroxide, cadmium carbonate, cadmium ethylate, barium oxide, barium hydroxide, barium hydrate, barium carbonate, barium ethylate, barium pentylate, aluminum oxide, aluminum propylate, lead oxide, lead hydroxide, lead carbonate, tin oxide, tin butylate, cobalt oxide, cobalt hydroxide, cobalt carbonate, cobalt pentylate, nickel oxide, nickel hydroxide, and nickel carbonate.

In some instances, the incorporation of certain ingredients, particularly carboxylic acids or metal carboxylates, such as, small amounts of the metal acetate or acetic acid, used in conjunction with the metal reactant will facilitate the reaction and result in an improved product. For example, the use of up to about 5% of zinc acetate in combination with the required amount of zinc oxide facilitates the formation of a zinc phosphorodithioate.

The preparation of metal phosphorodithioates is well known in the art and is described in a large number of issued patents, including U.S. Pat. Nos. 3,293,181; 3,397,145; 3,396,109 and 3,442,804, the disclosures of which are hereby incorporated by reference. Also useful as antiwear additives are amine derivatives of dithiophosphoric acid compounds, such as are described in U.S. Pat. No. 3,637,499, the disclosure of which is hereby incorporated by reference in its entirety.

The zinc salts are most commonly used as antiwear additives in lubricating oil in amounts of 0.1 to 10, preferably 0.2 to 2, wt. %, based upon the total weight of the lubricating oil composition. They may be prepared in accordance with known techniques by first forming a dithiophosphoric acid, usually by reaction of an alcohol or a phenol with $P_2S_5$ and then neutralizing the dithiophosphoric acid with a suitable zinc compound.

Mixtures of alcohols can be used, including mixtures of primary and secondary alcohols, secondary generally for imparting improved antiwear properties and primary for thermal stability. Mixtures of the two are particularly useful. In general, any basic or neutral zinc compound could be used, but the oxides, hydroxides, and carbonates are most generally employed. Commercial additives frequently contain an excess of zinc owing to use of an excess of the basic zinc compound in the neutralization reaction.

The zinc dihydrocarbyl dithiophosphates (ZDDP) are oil soluble salts of dihydrocarbyl esters of dithiophosphoric acids and can be represented by the following formula:

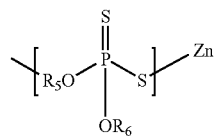

wherein $R_5$ and $R_6$ are as described in connection with the previous formula.

Especially preferred additives for use in the practice of the present invention include alkylated diphenylamines, hindered alkylated phenols, hindered alkylated phenolic esters, molybdenum dithiocarbamates, metallic phenates, metallic sulfurized phenates, metallic sulfonates, metallic alkyl salicylates.

Lubricant Compositions

Compositions, when they contain these additives, are typically blended into the base oil in amounts such that the additives therein are effective to provide their normal attendant functions. Representative effective amounts of such additives are illustrated in TABLE 1.

TABLE 1

| Additives | Preferred Weight % | More Preferred Weight % |
|---|---|---|
| V.I. Improver | 1-12 | 1-4 |
| Corrosion Inhibitor | 0.01-3 | 0.01-1.5 |
| Oxidation Inhibitor | 0.01-5 | 0.01-1.5 |
| Dispersant | 0.01-10 | 0.01-5 |
| Lube Oil Flow Improver | 0.01-2 | 0.01-1.5 |
| Detergent/Rust Inhibitor | 0.01-6 | 0.01-3 |
| Pour Point Depressant | 0.01-1.5 | 0.01-0.5 |
| Antifoaming Agent | 0.001-0.1 | 0.001-0.01 |
| Antiwear Agent | 0.001-5 | 0.001-1.5 |
| Seal Swellant | 0.1-8 | 01.-4 |
| Friction Modifier | 0.01-3 | 0.01-1.5 |
| Lubricating Base Oil | Balance | Balance |

When other additives are employed, it may be desirable, although not necessary, to prepare additive concentrates comprising concentrated solutions or dispersions of the subject additives of this invention, together with one or more of said other additives (said concentrate when constituting an additive mixture being referred to herein as an additive-package) whereby several additives can be added simultaneously to the base oil to form the lubricating oil composition. Dissolution of the additive concentrate into the lubricating oil can be facilitated by solvents and/or by mixing accompanied by mild heating, but this is not essential. The concentrate or additive-package will typically be formulated to contain the additives in proper amounts to provide the desired concentration in the final formulation when the additive-package is combined with a predetermined amount of base lubricant. Thus, the subject additives of the present invention can be added to small amounts of base oil or other compatible solvents along with other desirable additives to form additive-packages containing active ingredients in collective amounts of, typically, from about 2.5 to about 90 percent, preferably from about 15 to about 75 percent, and more preferably from about 25 percent to about 60 percent by weight additives in the appropriate proportions with the remainder being base oil. The final formulations can typically employ about 1 to 20 weight percent of the additive-package with the remainder being base oil.

All of the weight percentages expressed herein (unless otherwise indicated) are based on the active ingredient (AI) content of the additive, and/or upon the total weight of any additive-package, or formulation, which will be the sum of the AI weight of each additive plus the weight of total oil or diluent.

In general, the lubricant compositions of the invention contain the additives in a concentration ranging from about 0.05 to about 30 weight percent. A concentration range for the additives ranging from about 0.1 to about 10 weight percent based on the total weight of the oil composition is preferred. A more preferred concentration range is from about 0.2 to about 5 weight percent. Oil concentrates of the additives can contain from about 1 to about 75 weight percent of the additive reaction product in a carrier or diluent oil of lubricating oil viscosity.

In general, the additives of the present invention are useful in a variety of lubricating oil base stocks. The lubricating oil base stock is any natural or synthetic lubricating oil base stock fraction having a kinematic viscosity at 100° C. of about 2 to about 200 cSt, more preferably about 3 to about 150 cSt, and most preferably about 3 to about 100 cSt. The lubricating oil base stock can be derived from natural lubricating oils, synthetic lubricating oils, or mixtures thereof. Suitable lubricating oil base stocks include base stocks obtained by isomerization of synthetic wax and wax, as well as hydrocrackate base stocks produced by hydrocracking (rather than solvent extracting) the aromatic and polar components of the crude. Natural lubricating oils include animal oils, such as, lard oil, vegetable oils (e.g., canola oils, castor oils, sunflower oils), petroleum oils, mineral oils, and oils derived from coal or shale.

Synthetic oils include hydrocarbon oils and halo-substituted hydrocarbon oils, such as, polymerized and interpolymerized olefins, alkylbenzenes, polyphenyls, alkylated diphenyl ethers, alkylated diphenyl sulfides, as well as their derivatives, analogs, homologues, and the like. Synthetic lubricating oils also include alkylene oxide polymers, interpolymers, copolymers, and derivatives thereof, wherein the terminal hydroxyl groups have been modified by esterification, etherification, etc.

Another suitable class of synthetic lubricating oils comprises the esters of dicarboxylic acids with a variety of alcohols. Esters useful as synthetic oils also include those made from $C_5$ to $C_{12}$ monocarboxylic acids and polyols and polyol ethers.

Silicon-based oils (such as the polyalkyl-, polyaryl-, polyalkoxy-, or polyaryloxy-siloxane oils and silicate oils) comprise another useful class of synthetic lubricating oils. Other synthetic lubricating oils include liquid esters of phosphorus-containing acids, polymeric tetrahydrofurans, poly α-olefins, and the like.

The lubricating oil may be derived from unrefined, refined, rerefined oils, or mixtures thereof. Unrefined oils are obtained directly from a natural source or synthetic source (e.g., coal, shale, or tar and bitumen) without further purification or treatment. Examples of unrefined oils include a shale oil obtained directly from a retorting operation, a petroleum oil obtained directly from distillation, or an ester oil obtained directly from an esterification process, each of which is then used without further treatment. Refined oils are similar to unrefined oils, except that refined oils have been treated in one or more purification steps to improve one or more properties. Suitable purification techniques include distillation, hydrotreating, dewaxing, solvent extraction, acid or base extraction, filtration, percolation, and the like, all of which are well-known to those skilled in the art. Rerefined oils are obtained by treating refined oils in processes similar to those used to obtain the refined oils. These rerefined oils are also known as reclaimed or reprocessed oils and often are additionally processed by techniques for removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst. Natural waxes are typically the slack waxes recovered by the solvent dewaxing of mineral oils; synthetic waxes are typically the wax produced by the Fischer-Tropsch process. The resulting isomerate product is typically subjected to solvent dewaxing and fractionation to recover various fractions having a specific viscosity range. Wax isomerate is also characterized by possessing very high viscosity indices, generally having a VI of at least 130, preferably at least 135 or higher and, following dewaxing, a pour point of about −20° C. or lower.

The additives of the present invention are especially useful as components in many different fuel and lubricating oil compositions. The additives can be included in a variety of oils with lubricating viscosity, including natural and synthetic lubricating oils and mixtures thereof. The additives can be included in crankcase lubricating oils for spark-ignited and compression-ignited internal combustion engines. The compositions can also be used in gas engine lubricants, turbine lubricants, automatic transmission fluids, gear lubricants, compressor lubricants, metal-working lubricants, hydraulic fluids, and other lubricating oil and grease compositions. The additives can also be used in motor fuel compositions.

The advantages and the important features of the present invention will be more apparent from the following examples.

EXAMPLES

Four-Ball AntiWear Testing

The anti-wear properties of the mercaptobenzothiazole-epoxide reaction products in a fully formulated lubricating oil were determined in the Four-Ball Wear Test under the ASTM D 4172 test conditions. The testing for these examples was done on a Falex Variable Drive Four-Ball Wear Test Machine. Four balls are arranged in an equilateral tetrahedron. The lower three balls are clamped securely in a test cup filled with lubricant and the upper ball is held by a chuck that is motor-driven. The upper ball rotates against the fixed lower balls. Load is applied in an upward direction through a weight/lever arm system. Loading is through a continuously variable pneumatic loading system. Heaters allow operation at elevated temperatures. The three stationary steel balls are immersed in 10 milliliters of sample to be tested, and the fourth steel ball is rotated on top of the three stationary balls in "point-to-point contact." The machine is operated for one hour at 75° C. with a load of 40 kilograms and a rotational speed of 1,200 revolutions per minute. The fully formulated lubricating oil contained all the additives typically found in a motor oil (with different anti-wear agents as noted in Table 1) as well as 0.5 wt % cumene hydroperoxide to help simulate the environment within a running engine. The additives were tested for effectiveness in a motor oil formulation and compared to identical formulations with and without any zinc dithiophosphate.

The performance of some of these additives is superior to that of the comparative zinc dithiophosphate (ZDDP) in the four-ball wear test. See Table 1.

Cameron-Plint TE77 High Frequency Friction Machine Anti-Wear Testing

Another test used to determine the anti-wear properties of these products is the Cameron-Plint Anti-wear test based on a sliding ball on a plate. The specimen parts (6 mm diameter AISI 52100 steel ball of 800±20 kg/mm² hardness and hardened ground NSOH B01 gauge plate of RC 60/0.4 micron) are rinsed and then sonicated for 15 minutes with technical grade hexanes. This procedure is repeated with isopropyl alcohol. The specimens are dried with nitrogen and set into the TE77. The oil bath is filled with 10 mL of sample. The test is run at a 30 Hertz Frequency, 100 Newton Load, 2-35 mm Amplitude. The test starts with the specimens and oil at room temperature. Immediately, the temperature is ramped over 15 minutes to 50° C., where it dwells for 15 minutes. The temperature is then ramped over 15 minutes to 100° C., where it dwells for 45 minutes. A third temperature ramp over 15 minutes to 150° C. is followed by a final dwell at 150° C. for 15 minutes. The total length of the test is 2 hours. At the end of the test, the wear scar diameter on the 6 mm ball is measured using a Leica StereoZoom® Stereomicroscope and a Mitutoyo 164 series Digimatic Head.

Example 1

1-(2-benzothiazoylthio)-2-decanol

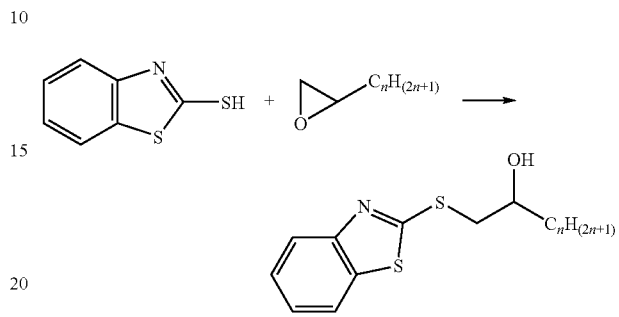

To a 100 mL 4-neck flask, (equipped with a mechanical stirrer, condenser, thermocouple probe, and a powder funnel) was charged 15.0 grams of 1,2-epoxydecane (obtained from Sigma-Aldrich, 95%). The epoxide was heated with stirring to 110° C. Mercaptobenzothiazole, 15.8 grams (Crompton), was added over 30 minutes. The reaction was stirred at 110° C. for 60 minutes and allowed to cool to room temperature. The reaction was taken up in hexanes and extracted with aqueous sodium hydroxide. Toluene and dilute acetic acid were added and the mixture was allowed to separate. The organic phase was dried over magnesium sulfate, filtered, and solvents were removed by rotary evaporation, to yield 24.7 grams of a light yellow liquid.

Example 2

1-(2-benzothiazoylthio)-2-dodecanol

To a 100 mL 4-neck flask, (equipped with a mechanical stirrer, condenser, thermocouple probe, and a powder funnel) was charged 18.4 grams of 1,2-epoxydodecane (95%). The epoxide was heated with stirring to 110° C. Mercaptobenzothiazole, 16.7 grams (Crompton), was added over 30 minutes. The reaction was stirred at 110° C. for 60 minutes and allowed to cool.

The orange liquid product was dissolved in 30 grams of hexanes and stirred. A precipitate formed, which was removed by filtration. The reaction mixture became cloudy upon standing overnight. The reaction mixture was filtered a second time, and the hexanes removed by rotary evaporation, to yield 29.5 grams of an amber liquid.

Example 3

1-(2-benzothiazoylthio)-2-tetradecanol

To a 100 mL 4-neck flask, (equipped with a mechanical stirrer, condenser, thermocouple probe, and a powder funnel) was charged 25.2 grains of 1,2-epoxytetradecane (obtained from Sigma-Aldrich, 85%). The epoxide was heated with stirring to 110° C. Mercaptobenzothiazole, 16.7 grams (Crompton), was added over 30 minutes. The reaction was stirred at 110° C. for 30 minutes, yielding 40.9 grams of a viscous yellow liquid that solidified upon standing at room temperature for three days.

Example 4

1-(2-benzothiazoylthio)-2-hexadecanol

To a 100 mL 4-neck flask, (equipped with a mechanical stirrer, condenser, thermocouple probe, and a powder funnel) was charged 28.2 grains of 1,2-epoxyhexadecane (obtained from Sigma-Aldrich, 85%). The epoxide was heated with stirring to 110° C. Mercaptobenzothiazole, 16.7 grams (Crompton), was added over 30 minutes. The reaction was stirred at 110° C. for 30 minutes, yielding 44.1 grains of a viscous yellow liquid that solidified upon cooling.

Example 5

1-(2-benzothiazoylthio)-2-octadecanol

To a 100 mL 4-neck flask, (equipped with a mechanical stirrer, condenser, thermocouple probe, and a powder funnel) was charged 25.0 grains of 1,2-epoxyoctadecane (obtained from Sigma-Aldrich, 85%). The epoxide was heated with stirring to 110° C. Mercaptobenzothiazole, 13.3 grains (Crompton), was added over 30 minutes. The reaction was stirred for 30 minutes, yielding 37.5 grains of a viscous yellow liquid that solidified upon cooling.

Example 6

2-(2-benzothiazoylthio)-cyclohexanol

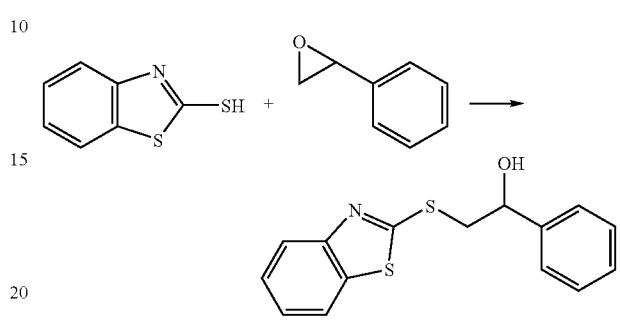

To a 500 mL 4 neck flask, (equipped with a mechanical stirrer, condenser, thermocouple probe, and a powder funnel) was charged 98.2 grams of cyclohexene oxide. The epoxide was heated with stirring to 110° C. Mercaptobenzothiazole (167.3 grams) was added over about 45 minutes. Addition was paced so as to keep the reaction temperature below 119° C. The reaction was then stirred at 110° C. for 60 minutes, and then allowed to cool to room temperature. Yield: 255.5 grams of a red liquid.

Example 7

2-(2-benzothiazoylthio)-cyclohexanol

To a 500 mL 4-neck flask, (equipped with a mechanical stirrer, condenser, thermocouple probe, and a powder funnel) was charged 98.2 grams of cyclohexene oxide (obtained from Sigma-Aldrich, 98%). The epoxide was heated with stirring to 110° C. Mercaptobenzothiazole, 167.3 grams (Crompton), was added over about 45 minutes. Addition was paced so as to keep the reaction temperature below 119° C. The reaction was then stirred at 110° C. for 60 minutes, and allowed to cool to room temperature. Yield: 255.5 grams of a red liquid.

Example 8

α-[(2-benzothiazoylthio)methyl]-benzenemethanol

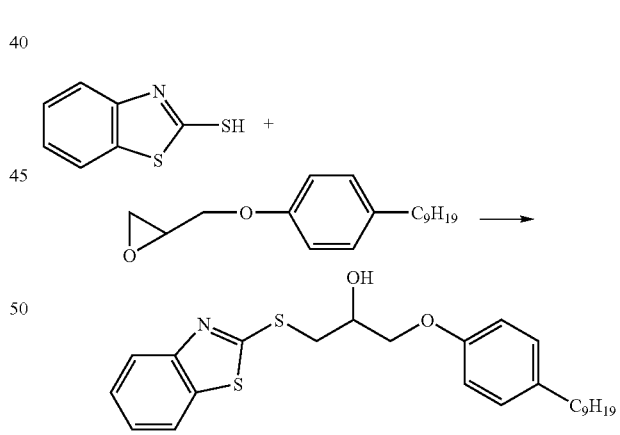

To a 100 mL 4-neck flask, (equipped with a mechanical stirrer, condenser, thermocouple probe, and a powder funnel) was charged 24.0 grains of styrene oxide (obtained from Sigma-Aldrich, 97%). The epoxide was heated with stirring to 110° C. Mercaptobenzothiazole, 33.4 grams (Crompton), was added over about 50 minutes. Addition was paced so as to keep the reaction temperature below 120° C., and generally below 115° C. The reaction was then stirred at 105° C. for 60 minutes and allowed to cool to room temperature. Yield: 55.3 grains of a viscous brown liquid.

Example 9

1-(2-benzoythiazoylthio)-3-(4-nonylphenoxy)-propan-2-ol

To a 100 mL 3-neck flask, (equipped with a mechanical stirrer, nitrogen inlet, and thermocouple probe) was charged 22.4 grains of glycidal 4-nonylphenyl ether (obtained from Sigma-Aldrich, technical grade) and 12.5 grains of mercaptobenzothiazole (Crompton). The mixture was heated with stirring to 105° C. After an exotherm to 135° C., the reaction was cooled and maintained at 110° C. for about 80 minutes. The product was allowed to cool to room temperature, taken up in xylenes, extracted with dilute sodium hydroxide, and washed twice with water. Solvent was removed by rotary evaporation to give the product, a viscous clear amber liquid.

Example 10

Reaction Product of Epoxidized 2-Ethylhexyl Tallate with Mercaptobenzothiazole

A 250 mL flask was charged with 57.38 grams of Drapex® 4.4 epoxidized 2-ethylhexyl tallate (Crompton), which was then heated to 110° C. Mercaptobenzothiazole, 28.06 grams, was added in 1-2 grain portions over 10 minutes. The temperature was maintained at 108-112° C. throughout the addition. The reaction was allowed to stir for an additional 25 minutes at 110° C., then taken up in xylenes and transferred to an addition funnel. Isopropanol was added, and the reaction mixture was extracted with 50 mL of 0.4% NaOH, and 50 mL water. Ethyl acetate was added, and the reaction mixture was extracted twice with dilute NaOH, and then with water. The reaction mixture was washed with water. Solvent was removed by rotary evaporation to give the 82.0 grams of a viscous clear amber liquid.

Example 11

Reaction Product of Epoxidized 2-Ethylhexyl Tallate with Mercaptobenzothiazole

A one liter resin kettle, equipped with an overhead stirrer, condenser, nitrogen inlet, thermocouple, and bottom out valve was charged with 252.1 grains of Drapex 4.4 epoxidized 2-ethylhexyl tallate (Crompton), and then heated to 110° C. while stirring. Mercaptobenzothiazole, 117.1 grams, was then added to the flask slowly over a period of 35 minutes. The reaction was then stirred at 110° C. for 1 hour. Xylenes were then added. The reaction mixture was then extracted with aqueous NaOH solution, and then washed twice with water at 70° C. Solvent was removed by rotary evaporation to yield 341.9 grams of a clear dark amber liquid.

Example 12

Reaction Product of Epoxidized Soybean Oil with Mercaptobenzothiazole

A 250 mL flask was charged with 52.06 grains of epoxidized soybean oil, which was then heated to 110° C. Mercaptobenzothiazole, 38.0 grains, was added in 1-2 grain portions over 120 minutes. The temperature was maintained at 108-112° C. throughout the addition. The reaction was allowed to stir for an additional 25 minutes at 110° C., then taken up in xylenes and transferred to an addition funnel. Isopropanol and ethyl acetate were added, and the reaction mixture was extracted twice with dilute NaOH, and then with water. Solvent was removed by rotary evaporation to give 86.1 grains of a viscous clear amber liquid.

Example 13

2-thiazoylthio-cyclohexanol

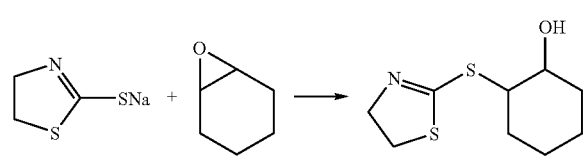

Cyclohexene oxide (0.078 mol) was added over one hour to 0.076 mmol of sodium mercaptothiazoline in water/isopropanol at 22° C. The reaction was stirred for one hour at 36° C. The product was taken up in ethyl acetate and extracted with dilute acetic acid. The product was washed with water, then isopropanol was added and the product was washed again with water. The product mixture was dried with magnesium sulfate, filtered, and stored at 2° C. The product was isolated as white crystals (3.88 grains, needles, mp 81-82.5° C.).

Example 14

1-thiazoylthio-2-dodecanol

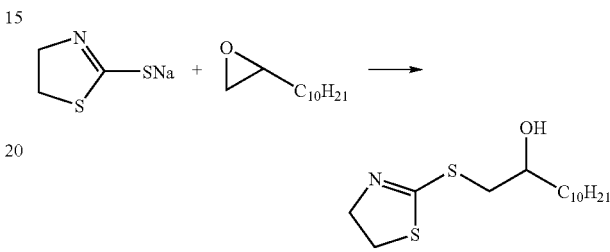

A 100 mL three-neck flask, equipped with an overhead stirrer, nitrogen inlet, and thermocouple, was charged with 2.19 grams of sodium hydroxide, 32 mL water, and then 6.38 grains of mercaptothiazoline. 1,2-Epoxydodecane was added by syringe over 25 minutes at 23° C. The reaction was heated to 70° C., and 30 mL isopropanol was added. The reaction was stirred at 65° C. for 30 min. and then transferred to a separatory funnel. The aqueous phase was removed. The material was diluted in isopropanol, ethyl acetate, and xylenes, and washed with dilute acetic acid, then washed twice with water. Solvent was removed by rotary evaporation to yield 16.1 grains of a clear oil that crystallized upon standing.

Example 15

1-benzimidazoylthio-2-dodecanol

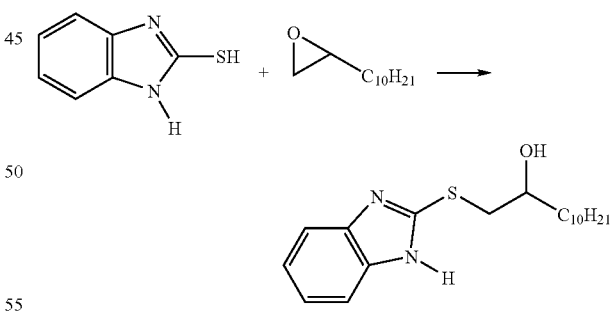

A 100 mL three-neck flask, equipped with an overhead stirrer, nitrogen inlet, and thermocouple, was charged with 1.52 grams of sodium hydroxide, 15 mL water, and 15 mL isopropanol. Mercaptobenzimidazole, 5.42 g, was added. The resulting clear solution was cooled to 4° C. 1,2-Epoxydodecane, 7.5 mL, was added, and the reaction was stirred at 4-6° C. for 30 minutes, then allowed to warm to 16° C. Glacial acetic acid, 2.2 mL, was added. The organic portion was taken up in xylenes and ethyl acetate and washed twice with water. Solvent was removed by rotary evaporator to yield 6.3 grams of an oil that solidified upon standing into shiny white flakes.

Example 16

1-(2-benzothiazoylthio)-3-butoxy-propan-2-ol

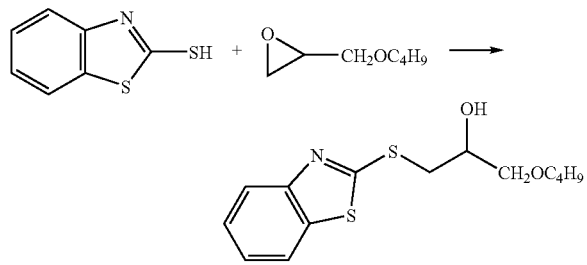

A 100 mL flask was charged with 46 grains of a 25 wt % solution of sodium mercaptobenzothiazole. Butyl glycidal ether was then added to this solution slowly at 23° C. This mixture was then stirred at 25° C. for 2.0 hours. The reaction mixture was then brought to a pH of 9 with acetic acid and extracted into xylenes. The xylenes solution was then washed twice with water at 75° C. Volatiles were removed by rotary evaporation to give 15.7 grams of a yellow liquid.

In view of the many changes and modifications that can be made without departing from principles underlying the invention, reference should be made to the appended claims for an understanding of the scope of the protection to be afforded the invention.

What is claimed is:

1. The compound

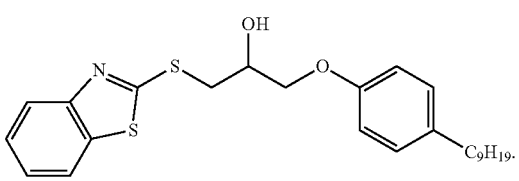

TABLE 2

Anti-Wear Test Data

| Ex. No. | AW Chemical Name | Four Ball | | Cameron Plint | | |
| | | Ave. of Scar (mm) | # of repetitions | Ave. Ball Scars (mm) | Ave. Plate Scars Depth (μm) | # of repetitions |
| --- | --- | --- | --- | --- | --- | --- |
| A | ZDDP 1% (comparative) | 0.481 | 49 | 0.424 | 1.79 | 43 |
| B | No Anti-wear (comparative) | 0.794 | 40 | 0.754 | 15.54 | 52 |
| 1 | 1-(2-benzothiazoylthio)-2-decanol | 0.422 | 2 | 0.746 | 1.692 | 2 |
| 2 | 1-(2-benzothiazoylthio)-2-dodecanol | 0.415 | 2 | 0.845 | 1.970 | 2 |
| 3 | 1-(2-benzothiazoylthio)-2-tetradecanol | 0.470 | 2 | 0.847 | 3.006 | 2 |
| 4 | 1-(2-benzothiazoylthio)-2-hexadecanol | 0.513 | 3 | 0.828 | 1.651 | 2 |
| 5 | 1-(2-benzothiazoylthio)-2-octadecanol | 0.468 | 4 | 0.837 | 3.169 | 2 |
| 6 | 1-(2-benzothiazoylthio)-2-cyclohexanol | 0.401 | 2 | 0.439 | 2.904 | 2 |
| 7 | 1-(2-benzothiazoylthio)-2-cyclohexano | 0.430 | 3 | 0.766 | 2.697 | 2 |
| 8 | α-[(2-benzothiazolylthio)-methyl]-benzenemethanol | 0.398 | 2 | | | |
| 9 | 1-(2-benzothiazoylthio)-3-(4-nonylphenoxy)-propan-2-ol | 0.388 | 2 | 0.777 | 6.428 | 2 |
| 10 | Reaction product of epoxidized 2-ethylhexyl tallate with mercaptobenzothiazole | 0.376 | 2 | | | |
| 11 | Reaction product of epoxidized 2-ethylhexyl tallate with mercaptobenzothiazole | 0.369 | 2 | 0.622 | 2.708 | 2 |
| 12 | Reaction product of epoxidized soybean oil with mercaptobenzothiazole | 0.375 | 2 | | | |
| 13 | 2-thiazoylthio-cyclohexanol | 0.448 | 2 | | | |
| 14 | 1-thiazoylthio-2-dodecanol | 0.424 | 2 | | | |
| 15 | 1-benzimidazoyl-2-dodecanol | 0.609 | 3 | | | |
| 16 | 1-(2-benzothiazoylthio)-3-butoxy-propan-2-ol | 0.562 | 2 | | | |

2. The compound
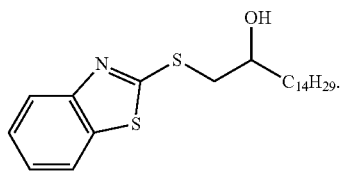
3. The compound
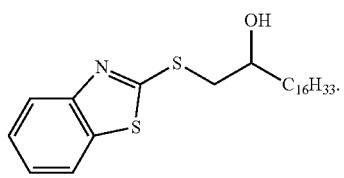
4. The compound
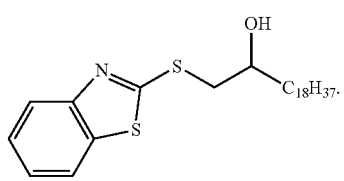
5. The compound
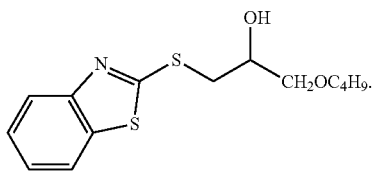
6. The compound
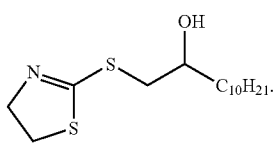
7. The compound
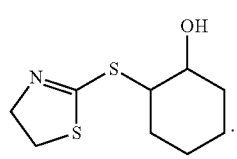
* * * * *